(12) United States Patent
Wettling et al.

(10) Patent No.: US 7,399,404 B2
(45) Date of Patent: Jul. 15, 2008

(54) REDUCTION OF THE CONTENT OF COMPOUNDS CONTAINING OXYGEN AND/OR NITROGEN IN MATERIAL FLOWS CONTAINING ISOBUTENE

(75) Inventors: Thomas Wettling, Limburgerhof (DE); Dirk Borchers, Ludwigshafen (DE)

(73) Assignee: BASF Aktiensegellschaft, Ludwigshafen (DE)

( * ) Notice: Subject to any disclaimer, the term of this patent is extended or adjusted under 35 U.S.C. 154(b) by 357 days.

(21) Appl. No.: 10/556,091

(22) PCT Filed: May 14, 2004

(86) PCT No.: PCT/EP2004/005200

§ 371 (c)(1),
(2), (4) Date: Nov. 9, 2005

(87) PCT Pub. No.: WO2004/101477

PCT Pub. Date: Nov. 25, 2004

(65) Prior Publication Data

US 2007/0106107 A1    May 10, 2007

(30) Foreign Application Priority Data

May 16, 2003   (DE) .............................. 103 22 153

(51) Int. Cl.
*C07C 7/12* (2006.01)
(52) U.S. Cl. .................... 208/254 R; 208/263; 585/820; 585/824
(58) Field of Classification Search ............. 208/254 R, 208/263; 585/820, 824
See application file for complete search history.

(56) References Cited

U.S. PATENT DOCUMENTS

| 5,120,881 | A | | 6/1992 | Rosenfeld et al. |
| 5,245,107 | A | * | 9/1993 | Yon et al. .................... 585/824 |
| 5,271,835 | A | * | 12/1993 | Gorawara et al. ........... 208/228 |
| 5,292,990 | A | * | 3/1994 | Kantner et al. .............. 585/820 |
| 5,427,689 | A | | 6/1995 | Kallenbach et al. |

FOREIGN PATENT DOCUMENTS

| DE | 39 14 817 | 11/1990 |
| EP | 0 582 901 | 2/1994 |
| EP | 0 628 575 | 12/1994 |
| SU | 1 011 624 | 4/1983 |
| WO | 93/10063 | 5/1993 |

* cited by examiner

*Primary Examiner*—Tam M. Nguyen
(74) *Attorney, Agent, or Firm*—Oblon, Spivak, McClelland, Maier & Neustadt, P.C.

(57) ABSTRACT

A process for reducing the content of oxygen-containing and/or nitrogen-containing compounds in streams having an isobutene content of at least 10% by weight, which comprises passing the stream in the liquid state at a temperature T [in K] and a linear velocity v [in cm/min] over a fixed bed of an acid-free zeolite having a mean pore size of from 0.3 to 1.5 nm, where the fixed bed has a length l [in cm] in the flow direction of the stream and T, v and l obey the relationship $$2^{(T-283\,K)/10\,K} \cdot l/v \leq 500\,\text{min},$$

is described. The process avoids the formation of isobutene oligomers.

10 Claims, No Drawings

REDUCTION OF THE CONTENT OF COMPOUNDS CONTAINING OXYGEN AND/OR NITROGEN IN MATERIAL FLOWS CONTAINING ISOBUTENE

The present invention relates to a process for reducing the content of oxygen-containing and/or nitrogen-containing compounds in streams having an isobutene content of at least 10% by weight.

In the thermal or thermal/catalytic cracking of natural gas, refinery gas or particular petroleum fractions, as is carried out, for example, in steam crackers, work-up of the cracking products gives, inter alia, mixtures of butadiene, butanes, n-butenes and isobutene, which are generally referred to as $C_4$ fractions.

Apart from the $C_4$-hydrocarbons, these $C_4$ fractions contain traces of various oxygen-containing and/or nitrogen-containing compounds. The type and amount of these impurities depend on the type and origin of the raw material used and on the technical conditions of the dissociation reaction. The further work-up of the $C_4$ fraction also influences the content of these impurities.

One use of $C_4$ fractions which is increasing in importance is the polymerization of the isobutene present in the $C_4$ fraction to give isobutene homopolymers or copolymers. Such polymerization processes are described, for example, in WO 93/10063 or EP 0 628 575 B1.

The presence of oxygen-containing and/or nitrogen-containing compounds in the starting material for the polymerization is undesirable since it leads to deactivation of the catalysts used or to an excessive consumption of catalyst.

It is known that catalyst poisons can be removed by adsorption on solid adsorbents such as molecular sieves or zeolites. Thus, DE-A 39 14 817 teaches passing a hydrocarbon feed mixture over molecular sieves having a pore diameter of greater than 4-15 Angström before it is oligomerized.

SU-A 1011624 describes a process for separating off carbonyl impurities from gaseous isobutene streams by adsorption on a magnesium-A zeolite.

Streams comprising isobutene cannot be readily purified by treatment with solid adsorbents. At active points on the surface of the adsorbent, isobutene very readily forms a tertiary carbocation onto which a further isobutene molecule can be added. Finally, an isooctene molecule is formed with reformation of the double bond or triisobutene or higher oligomers of isobutene are formed after addition of further isobutene molecules. The formation of isooctene or higher oligomers of isobutene is undesirable because of the loss of isobutene. In addition, a high content of isooctenes or higher oligomers of isobutene has an adverse effect on the polymerization behavior, since these compounds lead to premature chain termination and/or reduce the content of polyisobutene molecules having terminal vinylidene double bonds. The former makes the preparation of medium or high molecular weight isobutene polymers more difficult, while the latter makes it more difficult to prepare high-reactivity polyisobutenes, i.e. polyisobutenes having a high content of vinylidene double bonds.

It is an object of the present invention to provide a process for reducing the content of oxygen-containing and/or nitrogen-containing compounds in streams having an isobutene content of at least 10% by weight, in which the formation of isooctenes and higher oligomers of isobutene is suppressed.

We have found that this object is achieved by passing the stream in the liquid state at a temperature T [in K] and a linear velocity v [in cm/min] over a fixed bed of an acid-free zeolite having a mean pore size of from 0.3 to 1.5 nm, preferably from 0.5 to 1.2 nm, where the fixed bed has a length l [in cm] in the flow direction of the stream and T, v and l obey the relationship $$2^{(T-283\ K)/10\ K} \cdot l/v \leq 500\ \min,$$

preferably $$2^{(T-283\ K)/10\ K} \cdot l/v \leq 350\ \min.$$

According to the invention, it has been found that the formation of isobutene oligomers such as isooctenes can be suppressed by selection of a zeolite having a suitable pore size and control of the temperature and the contact time which in turn depends on the linear velocity of the stream and on the length of the fixed zeolite bed.

For the purpose of the present invention, the linear velocity or empty tube velocity v of the stream is the ratio of the volume flow [in cm$^3$/min] to the cross section of the fixed zeolite bed [in cm$^2$]. v is preferably in the range from 0.5 to 35 cm/min, in particular from 1 to 15 cm/min, particularly preferably from 1.5 to 10 cm/min.

T is preferably less than 40° C.; in particular, T is in the range from −30 to 30° C., particularly preferably from −25 to 20° C.

The pressure is selected so that the stream is present in the liquid state. The pressure is generally from 1 to 70 bar, preferably from 5 to 35 bar. It is advantageous to work at the pressure at which the stream is obtained in its production or is stored, transported or used further.

The stream treated according to the present invention contains at least 10% by weight of isobutene, preferably at least 20% by weight and in particular at least 40% by weight. The stream can also be essentially pure isobutene, i.e. a stream comprising more than 99% by weight of isobutene.

Typical oxygen-containing and nitrogen-containing compounds in the streams which are treated according to the present invention are aldehydes such as acetaldehyde, ketones such as acetone, alcohols such as methanol, ethanol, tert-butanol, ethers such as methyl tert-butyl ether, isopropyl tert-butyl ether, isobutyl tert-butyl ether, nitriles such as acetonitrile. Although streams having concentrations of oxygen-containing and nitrogen-containing compounds of up to 5% by weight can be treated by the process of the present invention, the treatment of streams containing more than 1000 ppm of these compounds is not advantageous because of the associated high consumption of zeolite or the frequent need for regeneration of the zeolite. In these cases, it is better to reduce the concentration of oxygen-containing and nitrogen-containing compounds to less than 1000 ppm by means of conventional methods before the process of the present invention is employed. The streams which are treated by the process of the present invention typically contain from 10 to 500 ppm of oxygen-containing and nitrogen-containing compounds.

In preferred embodiments, the stream further comprises hydrocarbons other than isobutene, e.g. $C_2$-$C_8$-hydrocarbons, in particular $C_4$-hydrocarbons. Thus, the stream can further comprise saturated hydrocarbons such as pentane, hexane, cyclohexane, methylcyclohexane or isooctane, or unsaturated hydrocarbons such as ethene or linear butenes. As starting materials for the process of the present invention, it is possible to use, for example, low-butadiene $C_4$ raffinates from crackers or $C_4$ fractions from the dehydrogenation of isobutane.

In other embodiments, the stream further comprises halogenated hydrocarbons, in particular chlorinated hydrocarbons such as chloromethane, dichloromethane, dichloroethane or trichloromethane, which serve as reaction solvent for a subsequent polymerization.

Zeolites, also referred to as molecular sieves, are crystalline aluminosilicates which have a highly ordered framework comprising a rigid three-dimensional network of $SiO_4$ and $AlO_4$ tetrahedra which are joined via shared oxygen atoms. To balance the electrovalence of the aluminum-containing tetrahedra, the zeolites contain cations. The aluminum in the lattice of the zeolites can be completely or partly replaced by other elements such as B, Ga, Fe, Cr, V, As, Sb, Bi or Be or mixtures thereof. The silicon can be replaced by another tetravalent element, e.g. Ge, Ti, Zr or Hf.

The zeolite used according to the present invention is acid-free, i.e. it does not contain any protons to balance the negative charge of the framework. The zeolite preferably contains sodium ions and/or alkaline earth metal ions such as calcium ions to balance the charge. On contact with particular chemicals, e.g. chlorides or fluorides, the surface of the zeolite can be permanently altered with formation of acidic centers. Contact with such chemicals should therefore be avoided. It is best to use a zeolite fresh from the factory for the process of the present invention. If irreversible contamination exceeds a particular limit, the zeolite should be replaced.

Zeolites can be synthesized by known methods, cf., for example, Ullmanns Enzyklopädie d. Techn. Chemie, 4th Edition, Vol. 17, pp. 9-17 (1983). The zeolites can be embedded in an oxidic binder matrix, e.g. a matrix comprising aluminum oxides, silicon dioxide, mixtures of finely divided silicon dioxide and aluminum oxide, titanium dioxide, zirconium dioxide or clay, and shaped to produce shaped bodies such as extrudates or pellets.

In the process of the present invention, zeolites having mean pore sizes of from 0.3 to 1.5 nm are used. The mean pore size is determined by the crystal structure and can be determined, for example, from X-ray structural data. Oxygen-containing and/or nitrogen-containing compounds cannot diffuse readily into zeolites having a relatively small mean pore size and are therefore insufficiently adsorbed. Zeolites having relatively large mean pore sizes lead to increased formation of isobutene oligomerization products on contact with the isobutene-containing streams.

Preferred zeolites are selected from among zeolite A, zeolite L, zeolite X and zeolite Y. Sodium zeolite A or sodium zeolite A in which the sodium ions are completely or partly replaced by calcium ions is particularly preferred.

It is occasionally advantageous to dry the stream and reduce the water content of the stream, e.g. to less than 5 ppm, preferably less than 1 ppm, before the zeolite treatment. In a preferred embodiment, a structured bed of two different zeolites is used. In this case, the stream is passed over a fixed bed which comprises a zeolite having a mean pore size of from about 0.3 to 0.4 nm upstream relative to the flow direction of the stream and a zeolite having a mean pore size of at least 0.5 nm downstream. The stream firstly comes into contact with the zeolite having a small pore size in a first zone, with water preferably being adsorbed. Larger oxygen- or nitrogen-containing molecules have a lesser tendency to be adsorbed in this first zone. Only in the subsequent second zone are these adsorbed by the large-pored zeolite. Water has a greater affinity for zeolites than do larger oxygen- or nitrogen-containing molecules. The embodiment described, in which water is removed preferentially in a first zone, has the advantage that, even when the zeolite has been saturated to an appreciable extent, no displacement of previously adsorbed oxygen- or nitrogen-containing molecules by water occurs.

The zeolite or the combination of zeolites is present in a fixed bed which is located in an adsorption column through which the stream is passed. The adsorption column is preferably vertical and the stream flows through it in the direction of gravity or counter to the direction of gravity. The length of the fixed bed in the flow direction is preferably from 2 to 15 times the (longest) diameter of the fixed bed. It is also possible to use a plurality of adsorption columns connected in series, which may, for example, be filled with different zeolites.

After a certain period of operation, the zeolite is saturated, i.e. its surface is occupied by oxygen-containing and/or nitrogen-containing compounds and no further adsorptive removal of these compounds from the stream takes place when the stream is passed through the bed. The zeolite can be regenerated by passing a stream of inert gas such as nitrogen over it at elevated temperature, e.g. from 150 to 250° C., and ambient pressure or reduced pressure. A typical regeneration cycle takes from about 4 to 24 hours. It is advantageous to provide at least two adsorption columns of which a first column is in the adsorption cycle while the other column is being regenerated. When the zeolite of the first column is saturated, the stream is rerouted and passed through the second adsorption column, so that the zeolite in the first column can be regenerated.

After the zeolite treatment according to the present invention, the streams generally have a total concentration of oxygen- and nitrogen-containing compounds of less than 20 ppm, in particular less than 10 ppm, with the concentrations of the individual contaminants generally each being less than 2 ppm, preferably less than 1 ppm. The streams which have been treated according to the present invention are particularly useful for preparing isobutene polymers. The preparation of isobutene homopolymers and copolymers is known per se, cf., for example, WO 93/10063 or EP 0 628 575 B1. Possible comonomers are, in particular, conjugated dienes such as butadiene and isoprene or vinylaromatic compounds such as styrene.

As polymerization catalysts for preparing isobutene homopolymers, preference is given to using catalysts based on boron trifluoride, in particular boron trifluoride complexes with at least one cocatalyst selected from among water, primary $C_1$-$C_5$-alkanols, secondary $C_3$-$C_5$-alkanols and ethers. The suitable cocatalysts are, for example, water, methanol, ethanol, 2-propanol, 1-propanol and/or tert-butyl methyl ether. The boron trifluoride catalyst complexes can be preformed before use or can be produced in situ in the polymerization reactor. Preference is given to using from 0.1 to 25 mmol, in particular from 0.5 to 10 mmol, of catalyst complex, calculated as boron trifluoride, per mole of olefin monomers.

The polymerization of isobutene is preferably carried out by a continuous process. This can be carried out in conventional reactors such as tube reactors, shell-and-tube reactors or stirred vessels. The polymerization is preferably carried out in a loop reactor, i.e. a tube or shell-and-tube reactor having continuous circulation of the reaction mixture, with the volume ratio of feed to circulating stream F/C generally being able to be varied in the range from 1:5 to 1:500, preferably in the range from 1:10 to 1:200.

The polymerization is advantageously carried out at temperatures below 0° C., preferably at temperatures in the range from 0 to −40° C., in particular in the range from 0 to −30° C. and particularly preferably in the range from −10 to −30° C. In general, the polymerization is carried out at a pressure in the range from 0.5 to 20 bar (absolute).

The residence time of the isobutene to be polymerized in the reactor is, depending on the reaction conditions and the desired properties of the polymer to be prepared, in the range from 1 to 120 minutes, preferably in the range from 5 to 60 minutes.

For the work-up, the reaction product mixture is advantageously introduced into a medium which deactivates the polymerization catalyst and thus stops the polymerization. This can be achieved using, for example, water, alcohols, ethers, acetonitrile, ammonia, amines or aqueous solutions of mineral bases such as alkali metal hydroxide and alkaline earth metal hydroxide solutions, solutions of carbonates of these metals and the like. Preference is given to stopping the polymerization by means of water at from 20 to 40° C., for example in the form of a pressure scrub. During the further course of the work-up, the polymerization mixture may be subjected to one or more extractions to remove residual amounts of catalyst, usually methanol or water scrubs. Unreacted isobutene, solvent and volatile isobutene oligomers are subsequently separated off by distillation. The bottoms are freed of residual solvent and monomers, for example by means of thin film evaporators, falling film evaporators, annular evaporators or Sambay evaporators, if appropriate with addition of water vapor or nitrogen gas.

The invention is illustrated by the following examples.

EXAMPLES 1 TO 6 AND COMPARATIVE EXAMPLES 7 AND 8

Isobutene-containing hydrocarbons having particular concentrations of oxygen-containing and nitrogen-containing impurities were passed through zeolite-filled columns. The concentration of the oxygen-containing and nitrogen-containing impurities and the content of isooctenes were subsequently measured. The results are summarized in the following table, in which all percentages are by weight and all ppm values are by weight (determined by GC analysis). The following abbreviations are used in the table: MTBE=methyl tert-butyl ether; IPTBE=isopropyl tert-butyl ether; IBTBE=isobutyl tert-butyl ether.

UOP 3A (EPG 1/16) is a potassium zeolite A having a mean pore size of from 0.3 nm from UOP. UOP 5A is a calcium zeolite A having a mean pore size of 0.5 nm. Grace 10A is a zeolite A having a mean pore size of 1.0 nm from Grace.

Two different adsorber columns were used (length/diameter): column A: 6000 mm/1500 mm; column B: 6400 mm/2100 mm

| Ex. | Column | Zeolite | Amount | Hydrocarbon | | Type | Impurities/content (before) | (after) |
|---|---|---|---|---|---|---|---|---|
| 1 | A | UOP 5A | 6 t | Isobutene | 17.30% | Methanol | 57 ppm | 3 ppm |
|   |   |         |     | 1-Butene  | 0.80%  | Isopropanol | 17 ppm | <1 ppm |
|   |   |         |     | 2-Butenes | 1.10%  | MTBE | 13 ppm | <1 ppm |
|   |   |         |     | Hexane    | 80.40% | IPTBE | 17 ppm | <1 ppm |
|   |   |         |     |           |        | IBTBE | 8 ppm | <1 ppm |
| 2 | A | UOP 5A | 6 t | Isobutene | 17.10% | Methanol | 51 ppm | 4 ppm |
|   |   |         |     | 1-Butene  | 0.79%  | Isopropanol | 16 ppm | <1 ppm |
|   |   |         |     | 2-Butenes | 1.17%  | MTBE | 13 ppm | <1 ppm |
|   |   |         |     | Hexane    | 80.47% | IPTBE | 17 ppm | <1 ppm |
|   |   |         |     |           |        | IBTBE | 5 ppm | <1 ppm |
| 3 | A | UOP 3A | 2 t | Isobutene | 17.00% | Methanol | 47 ppm | <1 ppm |
|   |   | UOP 5A | 4 t | 1-Butene  | 0.83%  | Isopropanol | 9 ppm | <1 ppm |
|   |   |         |     | 2-Butenes | 0.96%  | MTBE | 28 ppm | <1 ppm |
|   |   |         |     | Hexane    | 80.24% | IPTBE | 13 ppm | <1 ppm |
|   |   |         |     |           |        | IBTBE | 11 ppm | <1 ppm |
| 4 | B | UOP 3A | 4 t | Isobutene | >99%   | Acetonitrile | 7 ppm | <1 ppm |
|   |   | Grace 10A | 8 t | 1-Butene | 0.10% | Acetaldehyde | 2 ppm | <1 ppm |
|   |   |         |     | 2-Butenes | 0.20%  | Methanol | 9 ppm | <1 ppm |
|   |   |         |     |           |        | Ethanol | 17 ppm | <1 ppm |
|   |   |         |     |           |        | Acetone | 58 ppm | <1 ppm |
| 5 | B | UOP 3A | 4 t | Isobutene | >99%   | Acetonitrile | 7 ppm | <1 ppm |
|   |   | Grace 10A | 8 t | 1-Butene | 0.10% | Acetaldehyde | 2 ppm | <1 ppm |
|   |   |         |     | 2-Butenes | 0.20%  | Methanol | 11 ppm | <1 ppm |
|   |   |         |     |           |        | Ethanol | 18 ppm | <1 ppm |
|   |   |         |     |           |        | Acetone | 58 ppm | <1 ppm |
| 6 | B | Grace 10A | 12 t | Isobutene | >99% | Acetonitrile | 7 ppm | <1 ppm |
|   |   |         |      | 1-Butene  | 0.10% | Acetaldehyde | 2 ppm | <1 ppm |
|   |   |         |      | 2-Butenes | 0.20% | Methanol | 11 ppm | <1 ppm |
|   |   |         |      |           |       | Ethanol | 18 ppm | <1 ppm |
|   |   |         |      |           |       | Acetone | 58 ppm | 2 ppm |
| 7 | B | Grace 10A | 12 t | Isobutene | >99% | Acetonitrile | 8 ppm | <1 ppm |
|   |   |         |      | 1-Butene  | 0.10% | Acetaldehyde | 3 ppm | <1 ppm |
|   |   |         |      | 2-Butenes | 0.20% | Methanol | 9 ppm | <1 ppm |
|   |   |         |      |           |       | Ethanol | 19 ppm | <1 ppm |
|   |   |         |      |           |       | Acetone | 53 ppm | <1 ppm |
| 8 | B | Grace 10A | 12 t | Isobutene | >99% | Acetonitrile | 6 ppm | <1 ppm |
|   |   |         |      | 1-Butene  | 0.10% | Acetaldehyde | 5 ppm | <1 ppm |
|   |   |         |      | 2-Butenes | 0.20% | Methanol | 13 ppm | <1 ppm |
|   |   |         |      |           |       | Ethanol | 17 ppm | <1 ppm |
|   |   |         |      |           |       | Acetone | 61 ppm | 3 ppm |

-continued

| Ex. | Temperature | Pressure | Empty tube velocity | Isobutene dimers (ppm) | | |
|---|---|---|---|---|---|---|
| | | | | before | after | difference |
| 1 | 7° C. | 11 bar | 6.9 cm/min | 2315 | 2353 | 38 |
| 2 | 7° C. | 11 bar | 9.5 cm/min | 2127 | 2141 | 14 |
| 3 | 7° C. | 11 bar | 7.9 cm/min | 1248 | 1257 | 9 |
| 4 | 9° C. | 14 bar | 2.6 cm/min | <10 | 37 | max. 37 |
| 5 | 9° C. | 14 bar | 2.1 cm/min | <10 | 43 | max. 43 |
| 6 | 14° C. | 14 bar | 2.6 cm/min | <10 | 78 | max. 78 |
| 7 | 14° C. | 14 bar | 0.6 cm/min | <10 | 1330 | max. 1330 |
| 8 | 35° C. | 14 bar | 2.6 cm/min | <10 | 2708 | max. 2708 |

We claim:

1. A process for reducing the content of oxygen-containing and/or nitrogen-containing compounds in streams comprising:
passing a stream having an isobutene content of at least 10% by weight, in the liquid state at a temperature T [in K] and a linear velocity v [in cm/min] over a fixed bed of an acid-free zeolite having a mean pore size from 0.3 to 1.5 nm,
wherein the fixed bed has a length l [in cm] in a flow direction of a stream and T, v, and l obey the relationship $$2^{(T-283\ K)/10\ K} \cdot l/v \leq 500\ \text{min}.$$

2. A process as claimed in claim 1, wherein T is in a range from −30 to 30° C.

3. A process as claimed in claim 1, wherein v is in a range from 0.5 to 35 cm/mm.

4. A process as claimed in claim 1, wherein the stream further comprises hydrocarbons other than isobutene.

5. A process as claimed in claim 1, wherein the stream further comprises halogenated hydrocarbons.

6. A process as claimed in claim 1, wherein the zeolite comprises sodium ions and/or calcium ions to balance the charge.

7. A process as claimed in claim 1, wherein the zeolite is selected from the group consisting of zeolite A, zeolite L, zeolite X, and zeolite Y.

8. A process as claimed in claim 1, wherein the stream is dried prior to the zeolite treatment.

9. A process as claimed in claim 1, wherein the stream is passed through a fixed bed which comprises a zeolite having a mean pore size ranging from 0.3 to 0.4 nm upstream relative to the flow direction of the stream and a zeolite having a mean pore size at least 0.5 nm downstream.

10. A process as claimed in claim 1, wherein the steam is used for preparing isobutene polymers.

* * * * *

UNITED STATES PATENT AND TRADEMARK OFFICE
CERTIFICATE OF CORRECTION

PATENT NO.       : 7,399,404 B2  
APPLICATION NO.  : 10/556091  
DATED            : July 15, 2008  
INVENTOR(S)      : Wettling et al.

Page 1 of 1

It is certified that error appears in the above-identified patent and that said Letters Patent is hereby corrected as shown below:

On the title page, Item (73), the Assignee's name is incorrect. Item (73) should read:

-- (73) Assignee: BASF Aktiengesellschaft, Ludwigshafen (DE) --

Signed and Sealed this

Twenty-sixth Day of August, 2008

JON W. DUDAS  
*Director of the United States Patent and Trademark Office*

UNITED STATES PATENT AND TRADEMARK OFFICE
CERTIFICATE OF CORRECTION

PATENT NO. : 7,399,404 B2
APPLICATION NO. : 10/556091
DATED : July 15, 2008
INVENTOR(S) : Thomas Wettling et al.

It is certified that error appears in the above-identified patent and that said Letters Patent is hereby corrected as shown below:

Column 7, line 32, "from 0.5 to 35 cm/mm."
    should read -- from 0.5 to 35 cm/min. --.

Signed and Sealed this

Thirtieth Day of September, 2008

JON W. DUDAS
*Director of the United States Patent and Trademark Office*